(12) United States Patent
Santilli

(10) Patent No.: US 8,740,787 B2
(45) Date of Patent: Jun. 3, 2014

(54) RETRACTION OF THE LEFT ATRIAL APPENDAGE

(76) Inventor: Albert N. Santilli, Pepper Pike, OH (US)

( * ) Notice: Subject to any disclaimer, the term of this patent is extended or adjusted under 35 U.S.C. 154(b) by 1530 days.

(21) Appl. No.: 11/567,538

(22) Filed: Dec. 6, 2006

(65) Prior Publication Data

US 2007/0179345 A1 Aug. 2, 2007

Related U.S. Application Data

(60) Provisional application No. 60/762,993, filed on Jan. 27, 2006.

(51) Int. Cl.
*A61B 1/32* (2006.01)

(52) U.S. Cl.
USPC .......................................... 600/227

(58) Field of Classification Search
CPC ....... A61B 1/32; A61B 17/28; A61B 17/0206
USPC ............................ 606/227, 207; 600/201–246
See application file for complete search history.

(56) References Cited

U.S. PATENT DOCUMENTS

| | | | |
|---|---|---|---|
| 4,726,356 A * | 2/1988 | Santilli et al. ................. | 600/232 |
| RE34,150 E | 12/1992 | Santilli et al. | |
| 5,624,454 A * | 4/1997 | Palti et al. ...................... | 606/151 |
| 5,894,843 A * | 4/1999 | Benetti et al. .................. | 128/898 |
| 6,019,722 A * | 2/2000 | Spence et al. .................. | 600/210 |
| 6,099,468 A | 8/2000 | Santilli et al. | |
| 6,132,370 A * | 10/2000 | Furnish et al. ................. | 600/235 |
| 6,361,492 B1 * | 3/2002 | Santilli .......................... | 600/205 |
| 6,488,689 B1 | 12/2002 | Kaplan et al. | |
| 6,599,240 B2 * | 7/2003 | Puchovsky et al. ........... | 600/232 |
| 6,648,818 B2 * | 11/2003 | Cartier et al. .................. | 600/228 |
| 6,652,555 B1 | 11/2003 | Van Tassel et al. | |
| 6,730,022 B2 * | 5/2004 | Martin et al. .................. | 600/232 |
| 6,939,297 B2 * | 9/2005 | Gannoe et al. ................. | 600/232 |
| 7,014,609 B2 * | 3/2006 | Cartier et al. .................. | 600/228 |
| 7,220,228 B2 * | 5/2007 | Hu et al. ........................ | 600/210 |
| 7,235,049 B1 * | 6/2007 | Cohn .............................. | 600/235 |
| 7,294,104 B2 * | 11/2007 | Person .......................... | 600/227 |
| 2002/0177753 A1 * | 11/2002 | Dobrovolny ................... | 600/234 |
| 2005/0004652 A1 | 1/2005 | van der Burg et al. | |
| 2005/0149068 A1 * | 7/2005 | Williams et al. ............... | 606/151 |
| 2005/0149069 A1 | 7/2005 | Bertolero et al. | |
| 2005/0277959 A1 * | 12/2005 | Cosgrove et al. .............. | 606/151 |
| 2007/0149988 A1 * | 6/2007 | Michler et al. ................. | 606/157 |
| 2008/0033457 A1 * | 2/2008 | Francischelli et al. ........ | 606/142 |

* cited by examiner

*Primary Examiner* — Christopher Beccia
(74) *Attorney, Agent, or Firm* — Wayne D. Porter, Jr.

(57) ABSTRACT

A clamp is provided for attachment to the left atrial appendage (LAA). The clamp can be locked in a closed position so as to remain in place on the LAA. After being attached to the LAA, the clamp can be moved to a desired position such that the LAA can be retracted to a desired extent. The clamp can be held in any desired position, preferably by being connected to a thoracic retractor that is being used to retract the patient's sternum or ribs. A movable member is connected between the clamp and a stationary portion of the retractor. By locking the movable member in a fixed position relative to the stationary portion, the clamp can be maintained in a desired position and the LAA can be retracted as desired.

28 Claims, 3 Drawing Sheets

RETRACTION OF THE LEFT ATRIAL APPENDAGE

REFERENCE TO RELATED APPLICATIONS

Reference is made to U.S. patent application Ser. No. 11/315,799, filed Dec. 22, 2005 by Albert N. Santilli, et al., entitled Exclusion of the Left Atrial Appendage (the "Left Atrial Appendage Exclusion Patent"), the disclosure of which is incorporated herein by reference. Reference also is made to U.S. Provisional Patent Application Ser. No. 60/762,993, filed Jan. 27, 2006 by Albert N. Santilli, entitled Retraction of the Left Atrial Appendage, the disclosure of which is incorporated herein by reference and from which priority is claimed.

BACKGROUND OF THE INVENTION

1. Field of Invention

The present invention relates to cardiovascular surgery and, more particularly, to techniques for retraction and subsequent exclusion of the left atrial appendage.

2. Description of the Prior Art

Embolic stroke is a major cause of disability and death. The most common cause of embolic stroke emanating from the heart is thrombus formation due to atrial fibrillation. Atrial fibrillation is an arrhythmia of the heart that results in a rapid and chaotic heartbeat that produces lower cardiac output and irregular and turbulent blood flow in the vascular system. There are over five million people worldwide with atrial fibrillation, with about four hundred thousand new cases reported each year. Atrial fibrillation is associated with a 500 percent greater risk of stroke due to the condition. A patient with atrial fibrillation typically has a significantly decreased quality of life due, in large part, to the fear of a stroke, and the pharmaceutical regimen necessary to reduce that risk.

For patients who have atrial fibrillation and develop atrial thrombus therefrom, the clot normally occurs in the left atrial appendage (LAA) of the heart. The LAA is a cavity that is connected to the lateral wall of the left atrium between the mitral valve and the root of the left pulmonary vein. The LAA normally contracts with the rest of the left atrium during a normal heart cycle, thus keeping blood from becoming stagnant therein. However, the LAA, like the rest of the left atrium, does not contract in patients experiencing atrial fibrillation due to the discoordinate electrical signals associated with atrial fibrillation. As a result, thrombus formation is predisposed to form in the stagnant blood within the LAA. Of the patients with atrial thrombus, a large majority have the atrial thrombus located within the LAA. The foregoing suggests that the elimination or containment of the thrombus formed within the LAA of patients with atrial fibrillation would significantly reduce the incidence of stroke in those patients.

Pharmacological therapies for stroke prevention such as oral or systemic administration of blood thinning agents, such as warfarin, coumadin or the like have been inadequate due to serious side effects of the medications (e.g. an increased risk of bleeding) and lack of patient compliance in taking the medication.

As an alternative to drug therapy, invasive surgical procedures for closing or altering the LAA have been proposed. For example, U.S. Pat. No. 6,652,555 discloses a barrier device in the form of a membrane for covering the ostium of the LAA to prevent blood clots in the LAA from escaping and entering the blood stream. Published U.S. Patent Application No. 2005/0004652 discloses an occlusion device for inhibiting compression of the LAA in which tissue in-growth onto the occlusion member is provided. Both of these devices are extremely invasive in that the LAA must be opened (usually during the course of open heart surgery) and a foreign device implanted therein. The implanting process itself is time consuming to perform and increases the risk of hemorrhage and infection.

Another approach has been to attempt to close the LAA by means of an externally applied device or instrument. For example, U.S. Pat. No. 6,488,689 discloses that closure of the LAA can be accomplished by a loop of material, such as a suture, wire, tape, mesh, or the like, which can be applied over the LAA and cinched in place to close the LAA. The '689 patent also discloses that closure can be accomplished by stapling, clipping, fusing, gluing, clamping, riveting, or the like. Published U.S. Patent Application Nos. 2005/0149068 and 2005/0149069 disclose several types of clamps that can be fitted about the LAA externally and the compressed against the LAA.

The Left Atrial Appendage Exclusion Patent discloses an externally applied exclusion device for the LAA that is easy to apply. The device in question will apply the proper amount of compressive force to exclude the LAA while minimizing or avoiding any stress concentrations that would lead to undesired tissue necrosis. Moreover, the device will avoid punctures that would lead to difficult-to-control bleeding.

Although externally applied devices and techniques, particularly those disclosed in the Left Atrial Appendage Exclusion Patent, offer a relatively simple and effective approach to the problem of excluding the LAA, a particular problem has not been addressed. This problem relates to properly grasping and positioning the LAA so that a suitable exclusion device can be applied thereto. Typically, a surgical assistant manually grasps the LAA and pulls outwardly. The LAA will be slightly stretched so that the exclusion device can be applied by the surgeon. A significant problem with this approach is that the LAA usually is very slippery due to the tactile qualities of its surface and due to the presence of fluids such as blood. This makes it quite difficult for the surgical assistant to grasp the LAA and maintain a proper grip. In addition, because the operating theater is quite small, the presence of the surgical assistant's hand means that the surgeon's access to the LAA is impeded. Impeded access to the LAA makes it more difficult and time-consuming for the surgeon to properly apply the exclusion device to the LAA.

Desirably, a technique would be available that would permit the LAA to be grasped readily. Preferably, any such technique would enable the LAA to be grasped firmly and retracted to any position desired by the surgeon while providing minimal interference with the surgeon's access to the LAA.

SUMMARY OF THE INVENTION

In response to the foregoing concerns, the present invention provides a new and improved technique to grasp and retract the LAA and thereafter maintain it in a desired position. The invention comprises a clamp that can be attached to the end of the LAA and locked in a closed position so as to remain in place on the LAA. Preferably the facing portions of the clamp are knurled or otherwise textured in order to enable the clamp to grasp the LAA more securely. The clamp can be held in a desired position in a number of ways, preferably by being adjustably attached to a thoracic retractor that is being used to retract the patient's sternum or ribs.

A typical retractor usable with the invention has opposed arms that are connected by a toothed crossbar. The arms each have a grip that engages a portion of the patient's sternum or ribs. In one embodiment of the invention, the clamp includes a rod that projects outwardly thereof. A rod that normally is attached to, or included as part of, the retractor can be connected to the rod projecting from the clamp by means of one or more universal clamps. In another embodiment, a removable vertically oriented rod can be connected to the retractor. The rod can be connected to the rod projecting from the clamp by means of a universal connecter. In yet another embodiment, an adjustable "gooseneck" is connected at one end to a housing that can be attached to the retractor. The gooseneck is attached at its other end directly to the clamp.

In each of the referenced embodiments, the clamp can be attached to the LAA and then retracted to a desired position where it can be locked in place and held there without human assistance. Not only does the clamp enable the LAA to be grasped securely and positioned as desired, but it also provides the surgeon enough room to work on the LAA without interference.

The foregoing and other features and advantages of the invention are more fully described in the accompanying specification and claims and illustrated in the accompanying drawings.

DESCRIPTION OF THE PREFERRED EMBODIMENT

Figure 3:
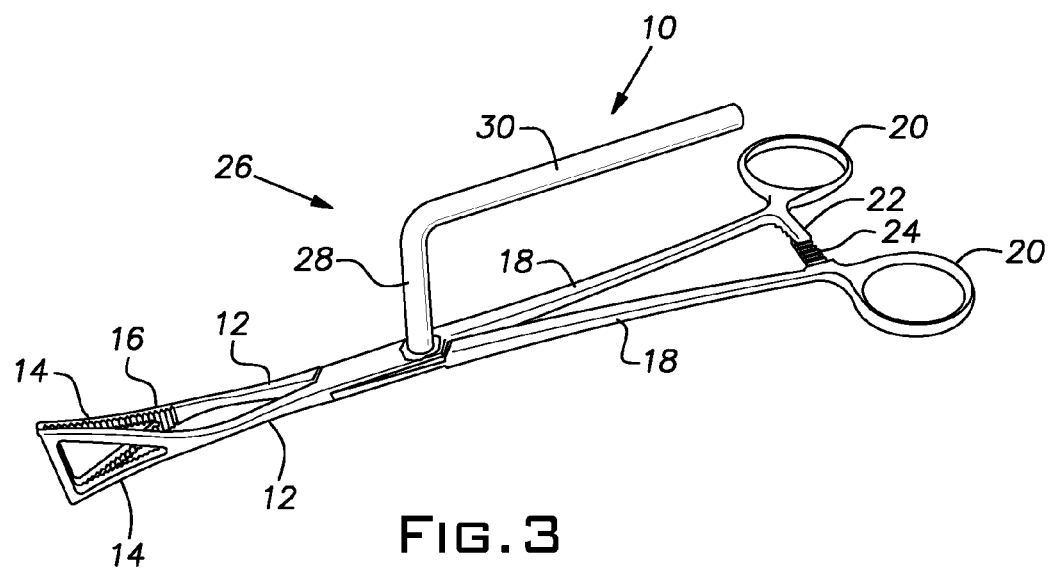
FIG. 3 is a perspective view of the clamp of FIG. 1 showing a rod connected to, and projecting from, the clamp.

Referring initially to FIG. 3, a clamp according to the invention is indicated by the reference numeral 10. The clamp 10 includes a pair of arms 12, each of which has an enlarged, flat-sided triangle-shaped jaw 14. The jaws 14 are knurled or otherwise textured as indicated by the reference numeral 16 on the sides that face each other. Handles 18 project from the arms 12. A finger loop 20 is disposed at the end of each of the handles 18. Tabs 22 with interlocking teeth 24 extend toward each other from a location adjacent the loops 24. A pivot pin (not shown) joins the arms 12 and the handles 18.

The clamp 10 includes an L-shaped rod 26. The rod 26 has legs 28, 30. Leg 28 is shorter than the leg 30 and is connected at one end to the side of one of the arms 12. The leg 30 extends away from the jaws 18 toward the loops 20 along a line intermediate the handles 18.

Preferably, the clamp 10 is a so-called Pennington tissue forceps that is commercially available in a variety of sizes and shapes. As illustrated, the arms 12 are generally parallel with each other when the clamp 10 is closed; the handles 18 diverge from each other in this position. A typical dimension for the jaws 14 is 14.7 cm in length.

Figure 1:
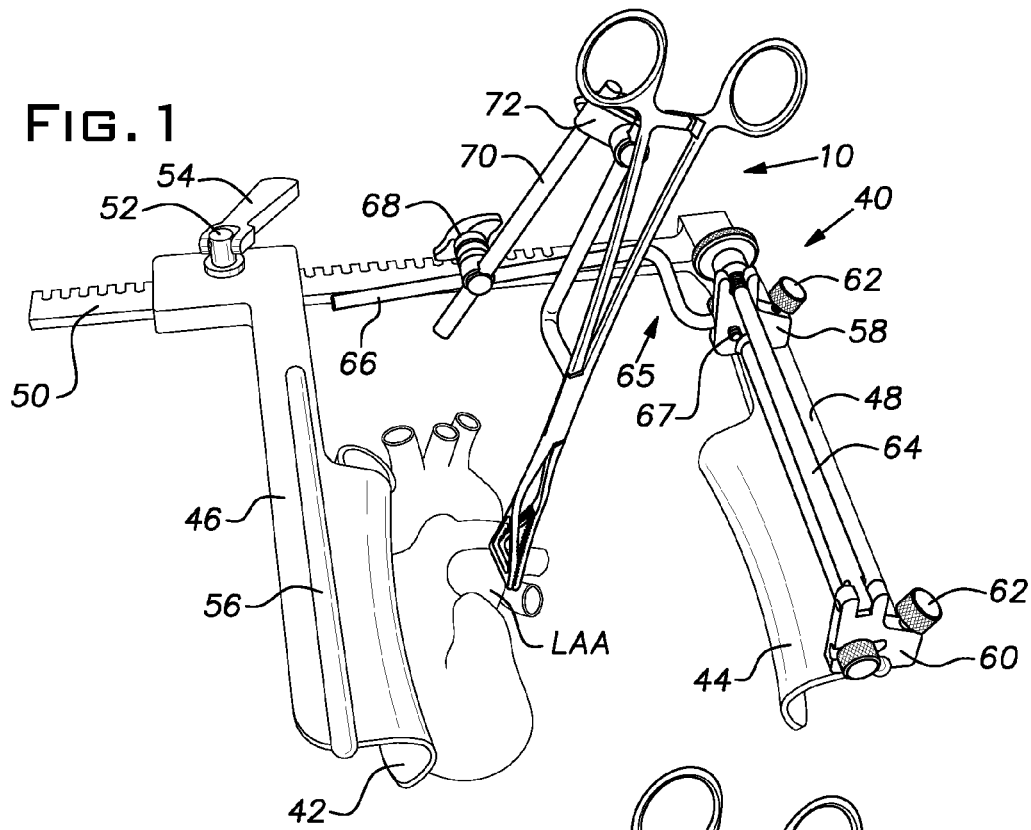
FIG. 1 is a perspective view of a clamp and retractor according to the invention showing the clamp in an extended position where it is grasping a patient's LAA.
Figure 2:
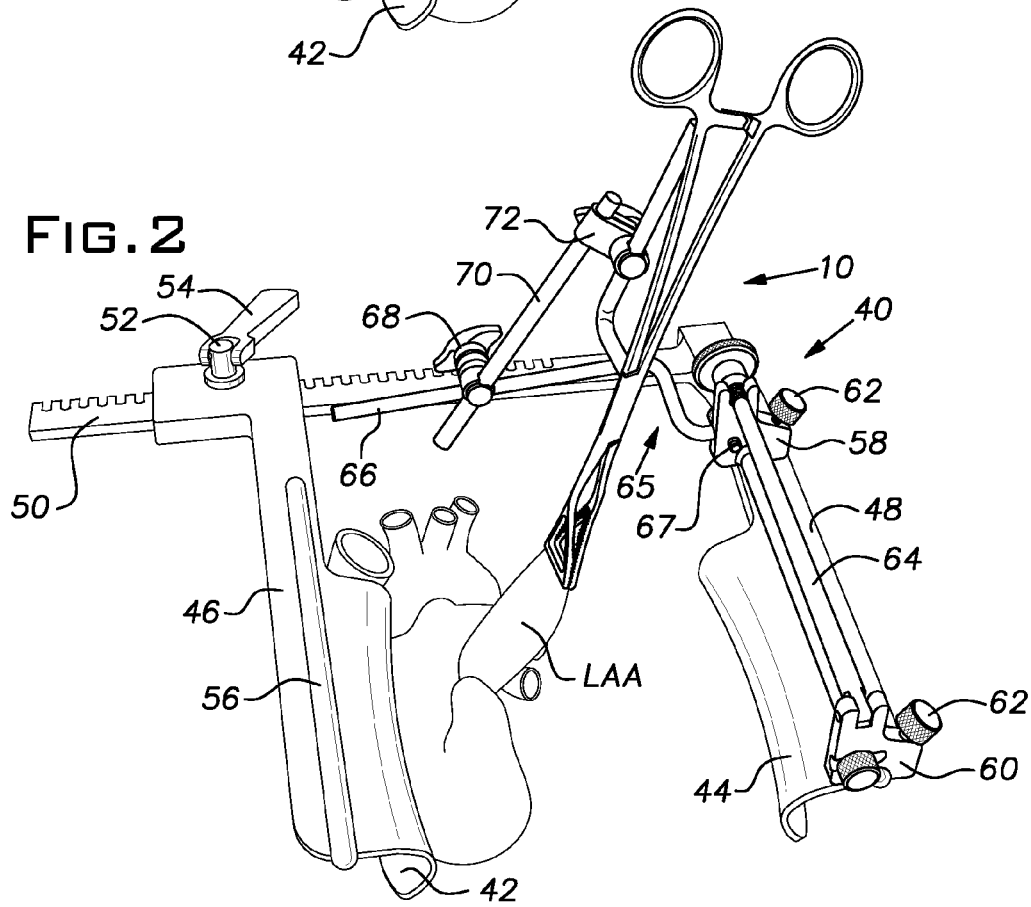
FIG. 2 is a view similar to FIG. 1 showing the clamp and the LAA in retracted positions.

Referring now to FIGS. 1 and 2, the clamp 10 is attached to a thoracic retractor 40. The retractor 40 is commercially available from Kapp Surgical Instrument, Inc., 4919 Warrensville Center Road, Cleveland, Ohio 44128 under the trademark COSGROVE. Reference is made to U.S. Pat. No. Re. 34,150, issued Dec. 29, 1992, to A. E. Santilli and D. M. Cosgrove III, the disclosure of which is incorporated herein by reference, for a full description of the retractor 40. Reference also is made to U.S. Pat. No. 6,099,468, issued Aug. 8, 2000 to Albert N. Santilli and Amit Patel, the disclosure of which is incorporated herein by reference, for a description of a similar retractor that includes additional features such as suture holders.

The retractor 40 has opposed grips 42, 44 disposed at the ends of arms 46, 48. The arm 48 is rigidly attached to a toothed crossbar 50. The arm 46 is movable along the crossbar 50 by means of a pinion 52 from which a handle 54 projects. A bar 56 is disposed atop each of the arms 46, 48. Brackets 58, 60 are mounted to a selected bar 56 and secured in position there by set screws 62. A first rod 64 is connected to the upper portion of the brackets 58, 60 and is held in a position above the selected arm 46, 48 in general alignment with the longitudinal axis of the arm 46, 48. A second, generally Z-shaped rod 65 is connected to the bracket 58. The rod 65 has an elongate portion 66 that is aligned generally parallel with the crossbar 50. The rod 65 is connected to the bracket 58 by fitting a slotted end of the rod 65 about a shoulder bolt 67 that can be tightened in place on the bracket 58.

A first universal clamp 68 is connected to the elongate portion 66 of the rod 65. A third, straight rod 70 is connected to the second rod 65 by means of the universal clamp 68. A second universal clamp 72, substantially identical to the first universal clamp 68, is mounted to the third rod 70. The leg 30 of the rod 26 also is connected to the universal clamp 72.

As can be seen from an examination of FIGS. 1 and 2, the universal clamps 68, 72 can be adjusted such that the jaws 14 are moved to a position to grasp the end of the LAA (FIG. 1). After the teeth 24 of the interlocking tabs 22 have been engaged to retain the jaws 14 firmly in place on the LAA, the clamp 10 can be moved to the right and/or upwardly (FIG. 2) in order to retract and slightly stretch the LAA. The surgeon then will have access to the LAA to apply an exclusion device without interference from a surgical assistant. As will be appreciated, the clamp 10 can be attached to the retractor 40 and adjusted to any desired position very quickly. Also, when work on the LAA has been completed, the clamp 10 and its supporting rods and clamps can be removed from the retractor in a matter of seconds.

Figure 4:
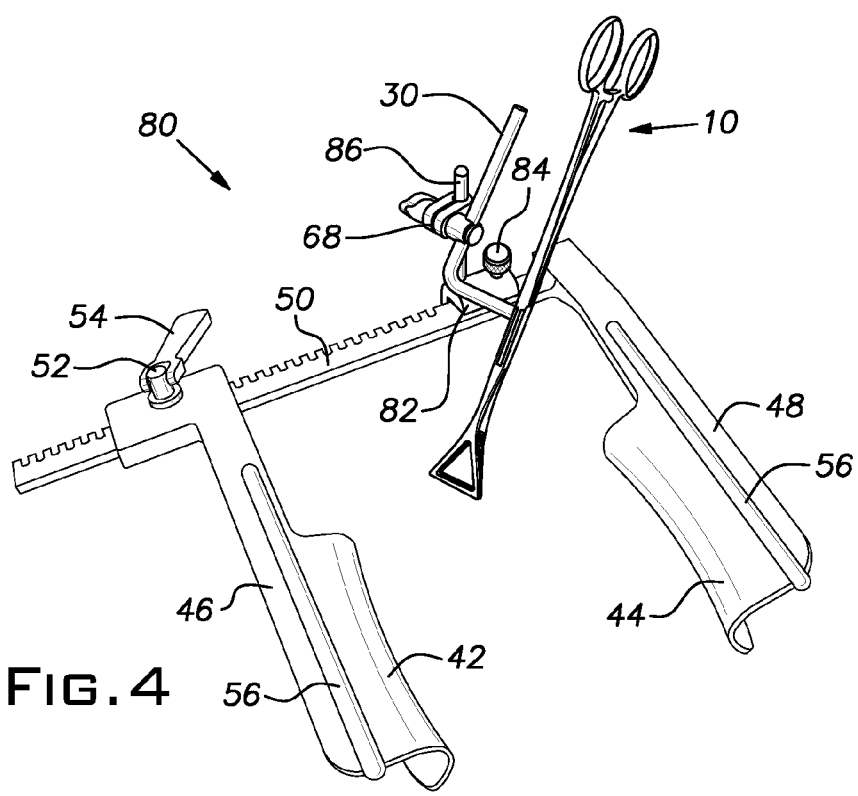
FIG. 4 is a perspective view of another embodiment of the invention showing the clamp of FIG. 1 attached to a retractor by a removable, vertically extending rod.

Referring now to FIG. 4, an alternative embodiment of the invention is indicated by the reference numeral 80. The embodiment 80 uses much of the structure of the previously described clamp 10 and retractor 40, and like reference numerals will be used where appropriate. The embodiment 80 has a block 82 that is adapted to fit over the toothed crossbar 50 and to be secured in place there by a set screw 84. A rod 86 extends vertically upwardly from the block 82. The universal clamp 68 is attached to the rod 86. The leg 30 of the rod 26 is connected to the rod 86 by means of the universal clamp 68.

Operation of the embodiment 80 is similar to operation of the first-described embodiment, except that the clamp 68 can only be moved vertically along the rod 86. The rod 86, however, can be moved horizontally along the crossbar 50 and secured in any desired position.

Figure 5:
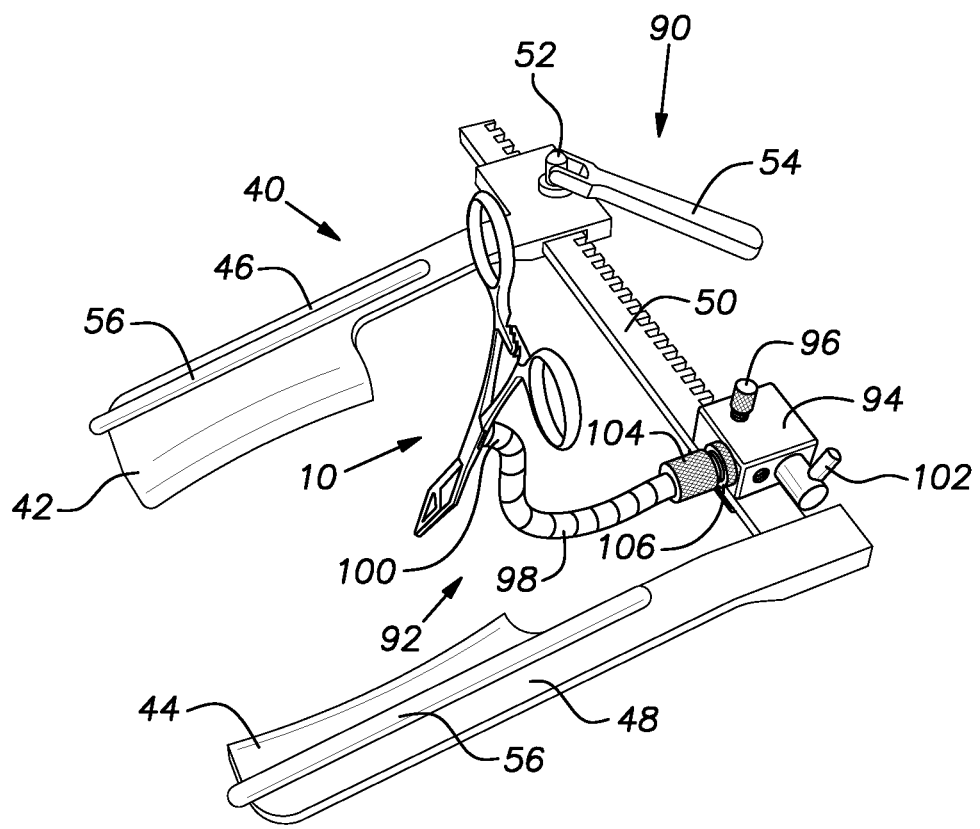
FIG. 5 is a perspective view of another embodiment of the invention showing the clamp of FIG. 1 connected to a retractor by a removable, adjustable gooseneck.

Referring now to FIG. 5, an alternative embodiment of the invention is indicated by the reference numeral 90. The embodiment 90 uses much of the structure of the previously described clamp 10 and retractor 40, and like reference numerals will be used where appropriate. The embodiment 90 uses a flexible "gooseneck" 92 to hold the clamp 10 in a desired position. Reference is made to U.S. Pat. No. 6,361, 492, issued Mar. 26, 2002 to Albert N. Santilli, the disclosure of which is incorporated herein by reference, for a full disclosure of the gooseneck 92. As more fully described in the '492 patent, a housing 94 is adapted to fit over the toothed crossbar 50 and to be secured in place there by a set screw 96. A plurality of small, tubular members 98 disposed in end-to-end relationship and an internal cable (not shown) extend from the housing 94. The distal end of the internal cable is connected to a fitting 100 that in turn is directly connected to the side of the clamp 10, as by soldering (the rod 26 is not used in this embodiment). A handle 102 carried by the housing 94 is used to loosen or tighten the internal cable. A nut 104 and a locknut 106 are used to pre-tension the internal cable.

As will be apparent from an examination of FIG. 5 and a review of the '492 patent, the housing 94 can be positioned on the crossbar 50 where desired. Upon loosening the handle 102, the fitting 100 with the clamp 10 attached can be moved to any desired position. After the desired position has been attained, the handle 102 can be moved so as to tighten the internal cable and lock the members 98 in the desired position. As with the other embodiments of the invention, the third embodiment 90 can be removed from the retractor 40 in a matter of seconds.

The block 82 and the housing 94 have been disclosed as being attached to the crossbar 50. If desired, these members could be attached to one of the arms 46, 48, presumably the fixed arm 46 because that arm typically would be positioned on the left side of the patient's chest. Also, the clamp 10 has been disclosed as a Pennington tissue forceps, but different types of clamps such as commercially available "Bulldog" clamps can be used as part of the invention. In addition, the second rod 65 has been disclosed as being connected to the bracket 58. It also is possible to connect the second rod 65 to the other bracket 60.

Although the present invention has been described in detail, it will be apparent to those skilled in the art that various changes and modifications can be made without departing from the true spirit and scope of the invention as hereinafter claimed. It is intended that all such changes and modifications be encompassed within the scope of the present claims.

What is claimed is:

1. A device for retracting the left atrial appendage (LAA) of a heart during the course of a cardiovascular surgical procedure, comprising:
   a clamp, the clamp having jaws that are movable between a first, closed position and a second, open position, the jaws in the closed position configured for clamping the LAA between them and the jaws in the open position being released from the LAA;
   a rod that projects outwardly from the clamp;
   means for engaging the rod and retracting the clamp to a desired retracted position relative to the heart while the jaws are in the closed position and are clamped to the LAA; and
   means for holding the clamp in the desired retracted position while the jaws are in the closed position and are clamped to the LAA.

2. The device of claim 1, wherein the clamp is of the Pennington tissue forceps type.

3. The device of claim 2, wherein the LAA-engaging portions of the jaws are knurled or otherwise textured.

4. The device of claim 1, wherein the means for engaging the rod and retracting the clamp to a desired retracted position relative to the heart while the jaws are in the closed position and are clamped to the LAA and the means for holding the clamp in the desired retracted position while the jaws are in the closed position and are clamped to the LAA includes:
   a thoracic retractor, the retractor being engageable with a patient's sternum or ribs to retract the sternum or ribs, the retractor, while retracting the sternum or ribs, having a stationary portion that remains stationary during the surgical procedure; and
   a movable member, the movable member being connected to the rod, the movable member also being connected to the stationary portion and movable relative thereto, the movable member capable of being locked in a desired position relative to the stationary portion.

5. The device of claim 4, wherein:
   the rod is L-shaped; and
   the movable member includes a first universal clamp that connects the L-shaped rod and the thoracic retractor.

6. The device of claim 5, further comprising:
   a second rod that is connected to the thoracic retractor and maintained in a fixed position relative thereto;
   a second universal clamp; and
   a third rod, wherein the first universal clamp is connected between the L-shaped rod and the third rod, and the second universal clamp is connected between the second rod and the third rod.

7. The device of claim 5, further comprising:
   a second rod;
   a second clamp to which the second rod is connected, the second clamp being connected to the thoracic retractor such that the second rod can be moved relative to the thoracic retractor and then locked in a fixed position relative to the thoracic retractor; and
   the first universal clamp being connected to the second rod.

8. The device of claim 4, wherein the movable member comprises an adjustable gooseneck connector having first and second ends, the clamp being connected to the first end of the gooseneck connector and the second end of the gooseneck connector being connected to the thoracic retractor.

9. A device for retraction of the left atrial appendage (LAA) of a heart during the course of a cardiovascular surgical procedure, comprising:
   a thoracic retractor, the retractor being engageable with a patient's sternum or ribs to retract the sternum or ribs, the retractor, while retracting the sternum or ribs, having a stationary portion that remains stationary during the surgical procedure; and
   a movable member, the movable member being connected to the stationary portion and movable relative thereto, the movable member capable of being locked in a desired fixed position relative to the stationary portion; and
   a clamp having a rod that projects outwardly from the clamp, the rod being connected to the movable member, the clamp having jaws that are movable between a first, closed position and a second, open position, the jaws in the closed position configured for clamping the LAA between them and the jaws in the open position being released from the LAA, the connection between the movable member and the stationary member and the connection between the rod and the movable member being such that the LAA can be stretched away from the heart when the clamp is in the closed position and the LAA can be held in that stretched position.

10. The device of claim 9, wherein the clamp is of the Pennington tissue forceps type.

11. The device of claim 10, wherein the LAA-engaging portions of the jaws are knurled or otherwise textured.

12. The device of claim 9, wherein:
   the rod is L-shaped; and the movable member includes a first universal clamp that connects the L-shaped rod and the thoracic retractor.

13. The device of claim 12, further comprising:
a second rod that is connected to the thoracic retractor and maintained in a fixed position relative thereto;
a second universal clamp; and
a third rod, wherein the first universal clamp is connected between the L-shaped rod and the third rod, and the second universal clamp is connected between the second rod and the third rod.

14. The device of claim 12, further comprising:
a second rod;
a second clamp to which the second rod is connected, the second clamp being connected to the thoracic retractor such that the second rod can be moved relative to the thoracic retractor and then locked in a fixed position relative to the thoracic retractor; and
the first universal clamp being connected to the second rod.

15. The device of claim 9, wherein the movable member comprises an adjustable gooseneck connector having first and second ends, the clamp being connected to the first end of the gooseneck connector and the second end of the gooseneck connector being connected to the thoracic retractor.

16. A device for retracting the left atrial appendage (LAA) of a heart during the course of a cardiovascular surgical procedure, comprising:
a clamp, the clamp having jaws that are movable between a first, closed position and a second, open position, the jaws in the closed position configured for clamping the LAA between them and the jaws in the open position being released from the LAA;
a rod that projects outwardly from the clamp;
means for engaging the rod and retracting the clamp to a desired retracted position relative to the heart while the jaws are in the closed position and are clamped to the LAA; and
means for holding the clamp in the desired retracted position while the jaws are in the closed position and are clamped to the LAA;
wherein the means for engaging the rod and retracting the clamp to a desired retracted position relative to the heart while the jaws are in the closed position and are clamped to the LAA and the means for holding the clamp in the desired retracted position while the jaws are in the closed position and are clamped to the LAA includes:
a thoracic retractor, the retractor being engageable with a patient's sternum or ribs to retract the sternum or ribs, the retractor, while retracting the sternum or ribs, having a stationary portion that remains stationary during the surgical procedure; and a movable member, the movable member being connected to the rod, the movable member also being connected to the stationary portion and movable relative thereto, the movable member capable of being locked in a desired position relative to the stationary portion.

17. The device of claim 16 wherein the clamp is of the Pennington tissue forceps type.

18. The device of claim 17, wherein the LAA-engaging portions of the jaws are knurled or otherwise textured.

19. The device of claim 16, wherein:
the rod is L-shaped; and
the movable member includes a first universal clamp that connects the L-shaped rod and the thoracic retractor.

20. The device of claim 19, further comprising:
a second rod that is connected to the thoracic retractor and maintained in a fixed position relative thereto;
a second universal clamp; and
a third rod, wherein the first universal clamp is connected between the L-shaped rod and the third rod, and the second universal clamp is connected between the second rod and the third rod.

21. The device of claim 19, further comprising:
a second rod;
a second clamp to which the second rod is connected, the second clamp being connected to the thoracic retractor such that the second rod can be moved relative to the thoracic retractor and then locked in a fixed position relative to the thoracic retractor; and
the first universal clamp being connected to the second rod.

22. The device of claim 16, wherein the movable member comprises an adjustable gooseneck connector having first and second ends, the clamp being connected to the first end of the gooseneck connector and the second end of the gooseneck connector being connected to the thoracic retractor.

23. A device for retraction of the left atrial appendage (LAA) of a heart during the course of a cardiovascular surgical procedure, comprising:
a thoracic retractor, the retractor being engageable with a patient's sternum or ribs to retract the sternum or ribs, the retractor, while retracting the sternum or ribs, having a stationary portion that remains stationary during the surgical procedure; and
a movable member, the movable member being connected to the stationary portion and movable relative thereto, the movable member capable of being locked in a desired fixed position relative to the stationary portion;
a clamp having an L-shaped rod that projects outwardly from the clamp, the L-shaped rod being connected to the movable member, the clamp having jaws that are movable between a first, closed position and a second, open position, the jaws in the closed position configured for clamping the LAA between them and the jaws in the open position being released from the LAA, the connection between the movable member and the stationary member and the connection between the rod and the movable member being such that the LAA can be stretched away from the heart when the clamp is in the closed position and the LAA can be held in that stretched position; and
a first universal clamp included as part of the movable member that connects the L-shaped rod and the thoracic retractor.

24. The device of claim 23, wherein the clamp is of the Pennington tissue forceps type.

25. The device of claim 24, wherein the LAA-engaging portions of the jaws are knurled or otherwise textured.

26. The device of claim 23, further comprising:
a second rod that is connected to the thoracic retractor and maintained in a fixed position relative thereto;
a second universal clamp; and
a third rod, wherein the first universal clamp is connected between the L-shaped rod and the third rod, and the second universal clamp is connected between the second rod and the third rod.

27. The device of claim 23, further comprising:
a second rod;
a second clamp to which the second rod is connected, the second clamp being connected to the thoracic retractor such that the second rod can be moved relative to the thoracic retractor and then locked in a fixed position relative to the thoracic retractor; and
the first universal clamp being connected to the second rod.

28. The device of claim 23, wherein the movable member comprises an adjustable gooseneck connector having first and second ends, the clamp being connected to the first end of the gooseneck connector and the second end of the gooseneck connector being connected to the thoracic retractor.

\* \* \* \* \*